(12) United States Patent
Swisa

(10) Patent No.: US 7,055,520 B2
(45) Date of Patent: Jun. 6, 2006

(54) DEVICE AND METHOD FOR DETECTING THE FLOW OF A GAS

(76) Inventor: David Swisa, 68/28 Zahal Street, 49 450 Petah Tikva (IL)

( * ) Notice: Subject to any disclaimer, the term of this patent is extended or adjusted under 35 U.S.C. 154(b) by 281 days.

(21) Appl. No.: 09/761,153

(22) Filed: Jan. 17, 2001

(65) Prior Publication Data

US 2003/0004427 A1    Jan. 2, 2003

(51) Int. Cl.
*A61M 15/00* (2006.01)

(52) U.S. Cl. .......................... 128/200.24; 128/202.22; 128/205.23; 128/203.28; 600/538; 600/539; 600/540; 600/541

(58) Field of Classification Search .......... 128/204.23, 128/200.24, 202.22, 205.23, 203.28, 205.17; 600/538, 540, 541, 539; 482/13; 116/307, 116/308

See application file for complete search history.

(56) References Cited

U.S. PATENT DOCUMENTS

| | | | | |
|---|---|---|---|---|
| 471,389 A * | 3/1892 | Lacey | ........................ | 600/540 |
| 3,635,213 A * | 1/1972 | LaHay | ........................ | 600/346 |
| 3,890,967 A * | 6/1975 | Elam et al. | ............ | 128/205.17 |
| 4,096,855 A * | 6/1978 | Fleury, Jr. | .................... | 600/540 |
| 4,158,360 A * | 6/1979 | Adams | ........................ | 600/538 |
| 4,171,804 A * | 10/1979 | Thead, Jr. | .................... | 482/13 |
| 4,233,990 A * | 11/1980 | Yardley | ...................... | 600/541 |
| 4,291,704 A * | 9/1981 | Petty et al. | ................ | 600/541 |
| 4,299,236 A * | 11/1981 | Poirier | ........................ | 600/541 |
| 4,324,260 A * | 4/1982 | Puderbaugh | ................ | 600/541 |
| 4,347,853 A * | 9/1982 | Gereg et al. | ................ | 600/538 |
| 4,350,167 A * | 9/1982 | Heimlich | .................... | 600/540 |
| 4,363,328 A * | 12/1982 | Poirier et al. | ............... | 600/541 |
| 4,441,506 A * | 4/1984 | McCombs et al. | .......... | 600/541 |
| 4,499,905 A * | 2/1985 | Greenberg et al. | .......... | 600/540 |
| 4,696,307 A * | 9/1987 | Montgieux | ................. | 600/534 |
| 5,253,651 A * | 10/1993 | Stockwell et al. | .......... | 600/538 |
| 5,320,107 A * | 6/1994 | O'Brien | ...................... | 600/538 |
| 5,509,406 A * | 4/1996 | Kock et al. | ............. | 128/203.14 |
| 5,520,167 A * | 5/1996 | Hamilton | ............... | 128/200.23 |
| 5,749,368 A * | 5/1998 | Kase | .......................... | 600/533 |
| 5,911,219 A * | 6/1999 | Aylsworth et al. | ..... | 128/205.23 |
| 5,984,872 A * | 11/1999 | Vriend | ........................ | 600/529 |
| 6,213,120 B1* | 4/2001 | Block et al. | ............ | 128/204.23 |
| 6,450,969 B1* | 9/2002 | Farr et al. | ................... | 600/538 |

* cited by examiner

*Primary Examiner*—Glenn K. Dawson
*Assistant Examiner*—Michael G. Mendoza

(57) ABSTRACT

A device for detecting the flow of a gas from an opening comprising a chamber with an inlet, the chamber carrying a pressure displaceable member with an inner face exposed to the interior of the chamber and an outer face exposed to the ambient pressure such that the member is displaced as a result of the differential of the pressures; and a method of using the device and a method of manufacturing the device.

4 Claims, 5 Drawing Sheets

DEVICE AND METHOD FOR DETECTING THE FLOW OF A GAS

FIELD OF INVENTION

The invention relates to a device and method for detecting the existence of a flow of gas into or out of an opening, more particularly, but not exclusively, the breathing of a subject.

BACKGROUND

One of the conventional methods of rapidly determining whether an unconscious person is alive is to check for the existance of breathing. At times this may be done under hospital conditions. At other times, such as at the site of armed conflicts, disasters or accidents, it must be done in the field.

Direct detection of breathing is unreliable because the respiration of an injured or ill person may be sporadic, irregular or so subtle as to be nearly imperceptible. Accordingly, medical science abounds with complex technology that detects, monitors and measures respiration.

There are many devices commonly in practice. One device used to detect breathing is a thermistor or thermocouple placed in or near the patient's airway so that the patient's breath passes over the temperature sensing device. Breathing gas entering the patient has a temperature that is generally lower than the exhaled gas.

A second device for measuring the airflow to and from a patient is a pneumotach sensor placed between a supply of breathing gas and the patient's airway. The pneumotach provides a known resistance to the flow. The patient's breathing capacity may increase the resistance, which is measured.

A third type of airflow meter is a nasal cannula meter which includes a pair of ports that insert into the nares of the patient. A hollow tubing carries a fraction of the total amount of breathing gas to a sensor. If the total area of the patient's nares relative to the total area of the ports is known, the meter can provide a quantitative measure of the patient's airflow.

A fourth method uses a microphone or pressure sensor mounted on the exterior of the patient's neck to detect sounds or throat vibrations generated by respiration.

A fifth method is to convert air flow to an oscillatory wave signal and measure its amplitude. See, for example, devices recently taught by Berthon Jones in U.S. Pat. Nos. 5,704, 345, 6,029,665 and 6,138,675.

Other devices found for monitoring or measuring breathing include those in which the air flow mechanically rotates a propeller, displaces a vane, causes rotation of a tube or moves a ball within a tube, each of which is measured and provides an indication of the respiratory function of the subject.

Prior art reflects many devices for monitoring breathing that rely on pressure measurement to evaluate respiratory function. In U.S. Pat. No. 5,970,801, Ciobanu, et al disclose a variable orifice flow sensor that measures air flow by use of a hinged flapper which deflects as a result of air flow and triggers pressure sensing taps.

Starr et al, in U.S. Pat. No. 6,017,315, shows a monitor for measuring respiration that uses a pressure sensitive sensor.

In U.S. Pat. No. 5,052,400, Dietz discloses a method and apparatus that detects breathing by means of a pressure capacitance transducer that develops pressure variations in response to breathing.

Riker, in U.S. Pat. No. 5,170,798, teaches a pulmonary function tester that uses a pressure transducer in the mouthpiece to measure ambient pressure prior to and after sensing the pressure created by a patient's pulmonary function.

As can be seen from the above, all of the devices in use for monitoring breathing do more than merely indicate the existence of respiration. Rather, each of them uses a complex sensing device to detect, monitor or measure respiration. Moreover, all of the devices and methods referred to above require complex and expensive machinery that is typically found only in medical facilities. Such devices are not customarily brought into the field and most certainly not to remote or rugged sites.

There does not exist a simple and portable mechanical device that reliably detects and displays the existence of breathing, particularly at very low levels, without relying upon relatively complex technology to do so.

SUMMARY OF THE INVENTION

An object of the present invention is to provide a fast, reliable and easy method to detect the flow of gas through an opening, more particularly, to detect the existence of breathing of a subject.

According to a broad aspect of the present invention, there is provided a device for detecting the flow of gas through at least one opening in an object comprising an inlet for pressurewise association with the opening, a chamber having an interior in pressurewise association with the inlet, and a pressure displaceable member having an inner face exposed to the pressure within the chamber and an outer face exposed to the ambient pressure such that the pressure displaceable member is displaced as a result of a differential in respective pressures of the chamber interior and the ambient pressure.

According to further features of the preferred embodiment of the invention, the inlet is associatable with the opening by an attaching member quickly attachable to the object, the attaching member adapted for pressurewise association with the opening, such that the inlet is in fluid communication with the opening when the attaching member is attached to the object.

According to further features of the preferred embodiment of the invention, the attaching member is adapted to be applied to the mouth and nose of a subject, to a tracheal intubation device, to an appliance on the face of a subject or to any opening from which the breath of a subject enters and exits the body.

According to still further features of the preferred embodiment of the invention, the chamber is in fluid communication with an outlet which may have the same flow capacity as the inlet or may be configured so as to restrict the flow therethrough to a greater degree than the flow is restricted by the inlet.

According to yet further features of the preferred embodiment of the invention, the pressure displaceable member is removably coupled to a visual indicator of displacements of the pressure displaceable member. The visual indicator comprises a movable element and a graduated scale which indicates the extent of the movement thereof.

According to yet further features of the preferred embodiment of the invention, the movable element is tensionably connected to the pressure displaceable member.

According to still further features of the preferred embodiment of the invention, the pressure displaceable member is operatively associated with a sensor thereby to indicate displacement of the pressure displaceable member.

The indication may be visible, audible or tactile and may be transmitted to a remote receptor.

According to still further features of the preferred embodiment of the invention, the pressure displaceable member is protected by a casing which is removably attached to the device.

There is further provided a method of detecting the existence of breathing of a subject comprising the steps of applying the device for detecting the flow of a gas to a subject and viewing the pressure displaceable member thereof for movement.

There is further provided a method of detecting the flow of gas from an opening comprising the steps of applying the device for detecting the flow of a gas to an opening in an object and viewing the pressure displaceable member thereof for movement.

There is further provided a method of manufacturing a device for detecting the flow of a gas comprising the steps of providing a chamber; creating an inlet in fluid communication with the chamber, and attaching to the chamber a pressure displaceable member having an inner face exposed to the interior of the chamber and an outer face exposed to the ambient pressure such that the member is displaced as a result of the differential of the pressures of the chamber interior and the ambient pressure.

The device described herein may be applied to any opening. Any flow of gas therethrough will be immediately apparent as a result of the movement of the pressure displaceable member. Moreover, the preferred embodiment of the invention will allow the immediate detection of the presence or absence of breathing of a subject, allowing appropriate action to be taken without the need for time consuming diagnostic tests or evaluations.

Other features of the preferred embodiments of the invention are rugged design, which allows it to be used in difficult conditions; small size and weight allowing easy portability; simplicity, which allows it to be effectively employed by those with little or no training; and its clear, immediate and unambiguous indication of the existence of a gas flow.

BRIEF DESCRIPTION OF DRAWINGS

With specific reference now to the drawings in detail, it is stressed that the particulars shown are by way of example and for the purposes of illustrative discussion of the preferred embodiment of the present invention only, and are presented in the cause of providing what is believed to be the most useful and readily understood description of the principles and conceptual aspects of the invention. In this regard, no attempt is made to show structural details of the invention in more detail that is necessary for a fundamental understanding of the invention, the description taken with the drawings making apparent to those killed in the art how the several forms of the invention may be embodied in practice. In the accompanying drawings

GENERAL DESCRIPTION OF PREFERRED EMBODIMENT

Figure 1:
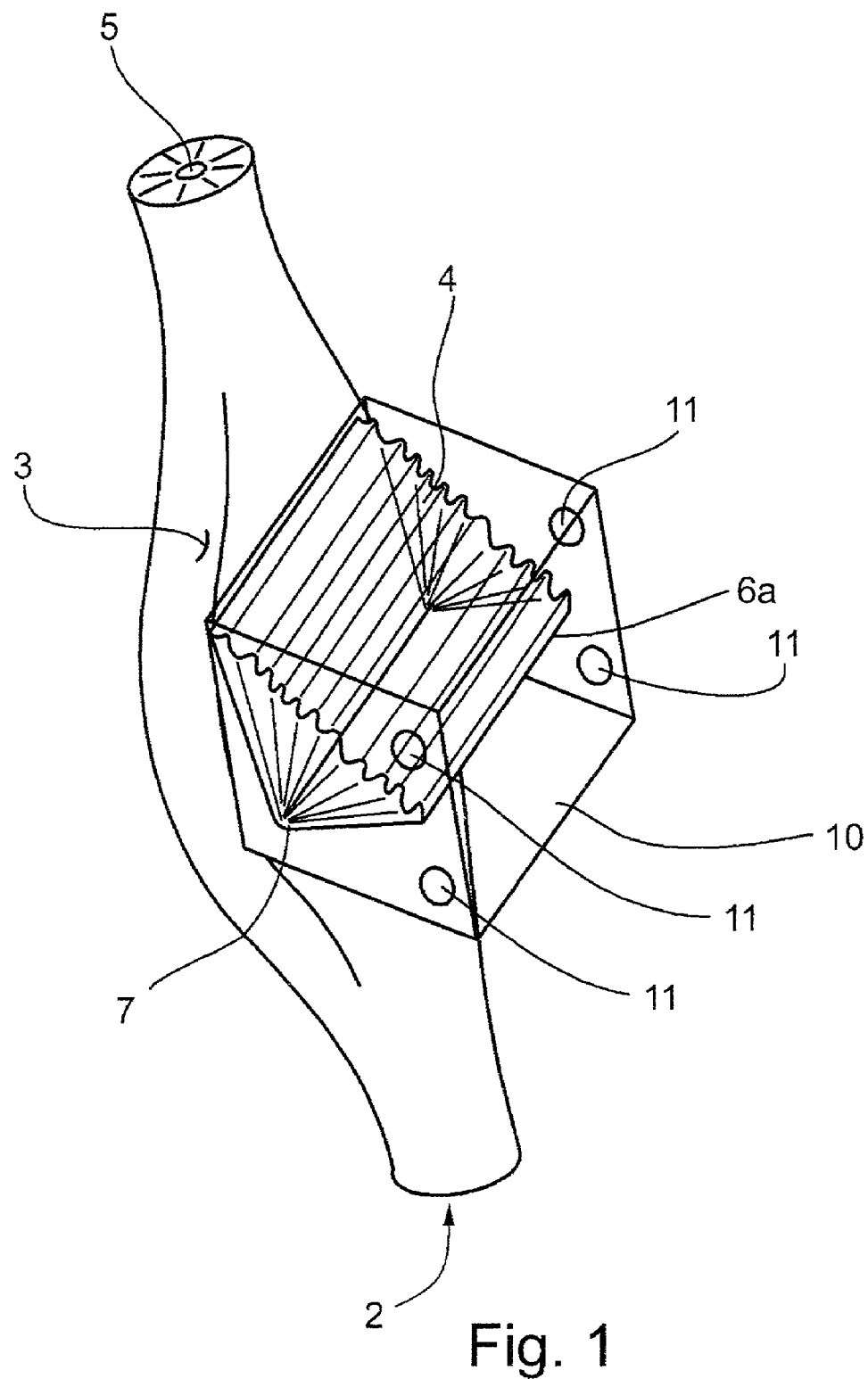
FIG. 1 is a perspective view of a device for detecting the flow of a gas consructed in accordance with a preferred embodiment of the invention.

Before explaining at least one embodiment of the invention in detail, it is to be understood that the invention is not limited in this application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

A preferred embodiment of the invention provides a device and method for detecting the existence of a flow of gas into or out of an opening. The device is particularly useful for detecting the breathing of a subject and is therefore described in that context below.

Reference is made to FIG. 1 which is a simplified diagram showing a perspective view of a device constructed in accordance with the preferred embodiment of the invention comprising three main elements: an inlet 2, a chamber 3, and a pressure displaceable member 4. The chamber 3 communicates fluidly with the inlet 2. The pressure displaceable member 4 is exposed on its inner face to the chamber 3. The chamber 3 is further in fluid communication with an outlet 5 which may have the same flow capacity as the inlet 2 or may be configured so as to restrict the flow of a gas to a greater degree than the flow is restricted by the inlet 2. The difference in the flow capacities between the inlet 2 and the outlet 5 influences the sensitivity of the device, The greater the difference, the greater the sensitivity.

Also shown in FIG. 1 is a protective casing 10 which encompasses the pressure displaceable member 4 and which contains holes 11 therein in order to expose the outer face of the pressure displaceable member 4 to the ambient pressure.

Figures 2, 2A:
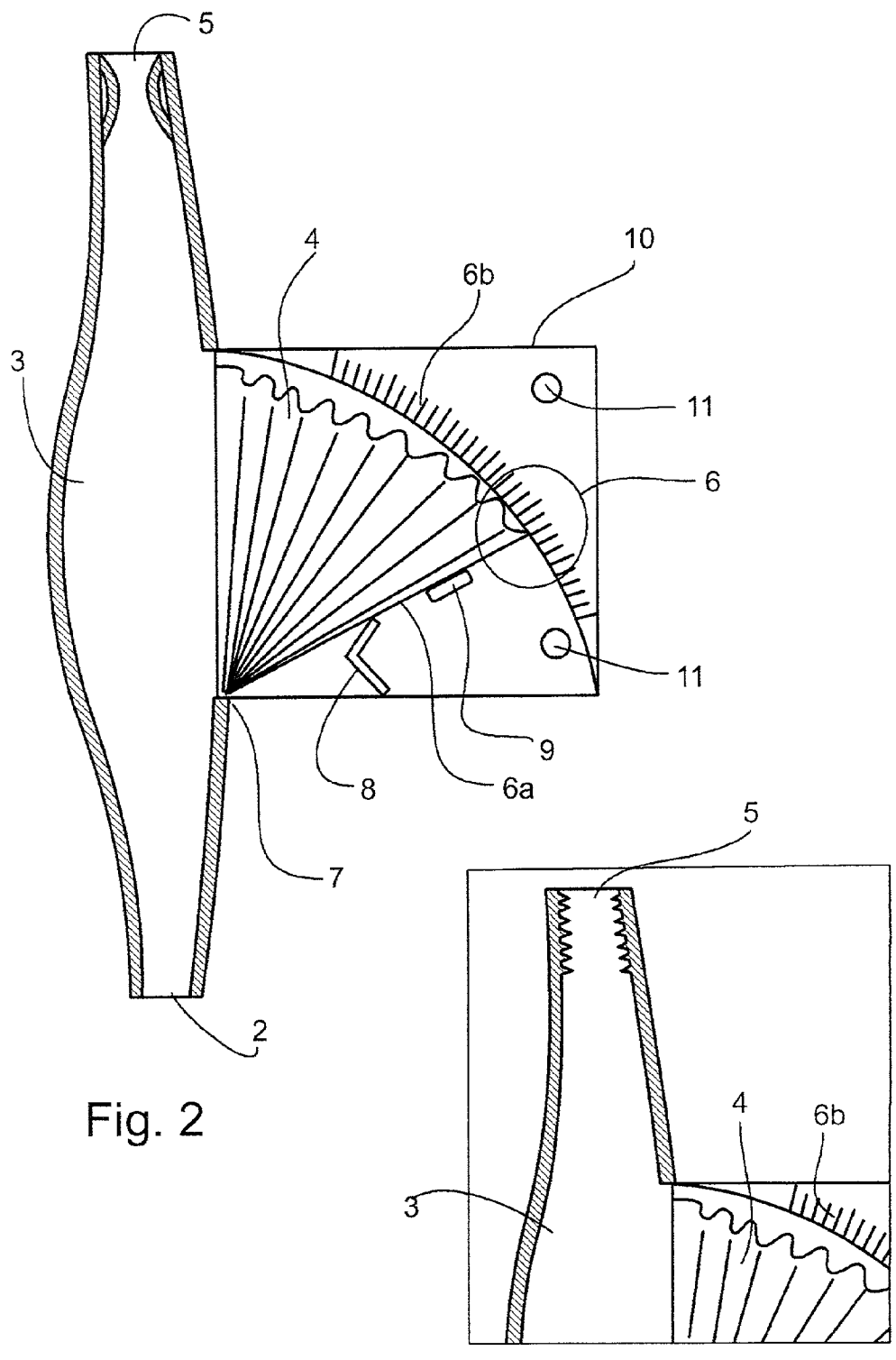
FIG. 2 is a section view of the device of FIG. 1 configured with the visual indicator, restricting means for adding resistance to the displacement of the visual indicator and a displacement sensor.
FIG. 2A is a section view of a portion of the device of FIG. 1 depicting with particularity the outlet.

FIG. 2 is a section view of the device configured with the inlet 2 in communication with the chamber 3 which in turn communicates with the ambient pressure via the outlet 5. It will be noted that in the preferred embodiment of the invention, the outlet is narrowed so as to have a smaller internal diameter than the inlet 2, thus restricting the flow capacity therethrough to be less than that of the inlet 2. It will be appreciated that the outlet may be configured in other manners so as to cause a restriction of the gas flow therethrough, such as by the insertion of baffles in the flow path or by having an irregular rather than a smooth interior wall. FIG. 2A depicts the outlet having a ribbed interior wall, restricting the flow capacity therethrough as a result of turbulence caused by the flow passing over the irregular surface.

Moreover, the outlet 5 may be configured to restrict the flow of gas to the same degree that the flow of gas is restricted by the inlet 2. This configuration may be preferable if the device is to remain applied to a subject for a protacted period of time in order to monitor the subject's breathing without causing an impediment to such breathing.

The pressure displaceable member 4 forms a part of the chamber 3, having its inner face exposed to the pressure within the chamber 3 and its outer face exposed to the ambient pressure. Removeably attached to the pressure displaceable member 4 is a visual indicator 6 comprising two component parts, a moveable element 6a and a scale 6b. The moveable element 6a is removably attached to the pressure displaceable member 4 in a hinged manner by a flexible strip 7. The visual indicator is useful for obtaining an indication of the respiratory volume of the subject. The movement of the moveable element 6a is restricted by a spring 8. If different degrees of restriction are needed for different applications, the tension of the spring 8 may be adjusted or springs of different tensions may be used. The device may be used without the spring 8 if desired.

Attached to the moveable element 6a is a sensor 9 that detects the displacement of the pressure displaceable member 4 and is capable of transmitting a signal indicating such displacement to a remote reciever. The pressure displaceable member 4, along with the visual indicator 6 and the sensor 9 are enclosed within a protective casing 10, which has holes 11 therein in order to expose the pressure displaceable member to the ambient pressure.

Figure 3:
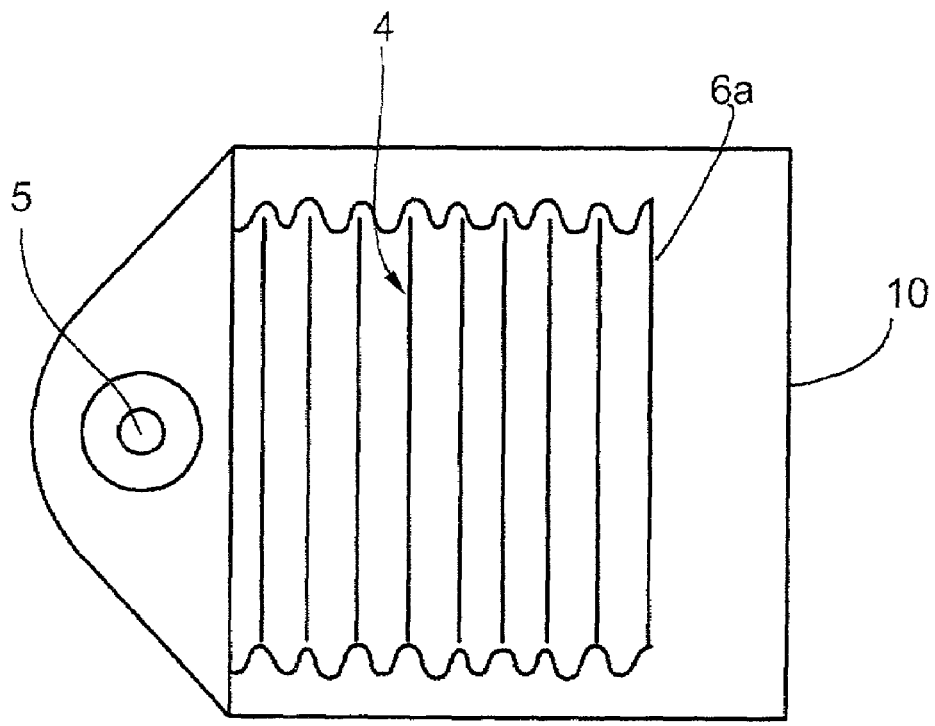
FIG. 3 is a top view of the device of FIG. 1.

FIG. 3 depicts the device from the top down, illustrating the configuration of the outlet 5 narrowed as shown in FIG. 2.

Figure 4:
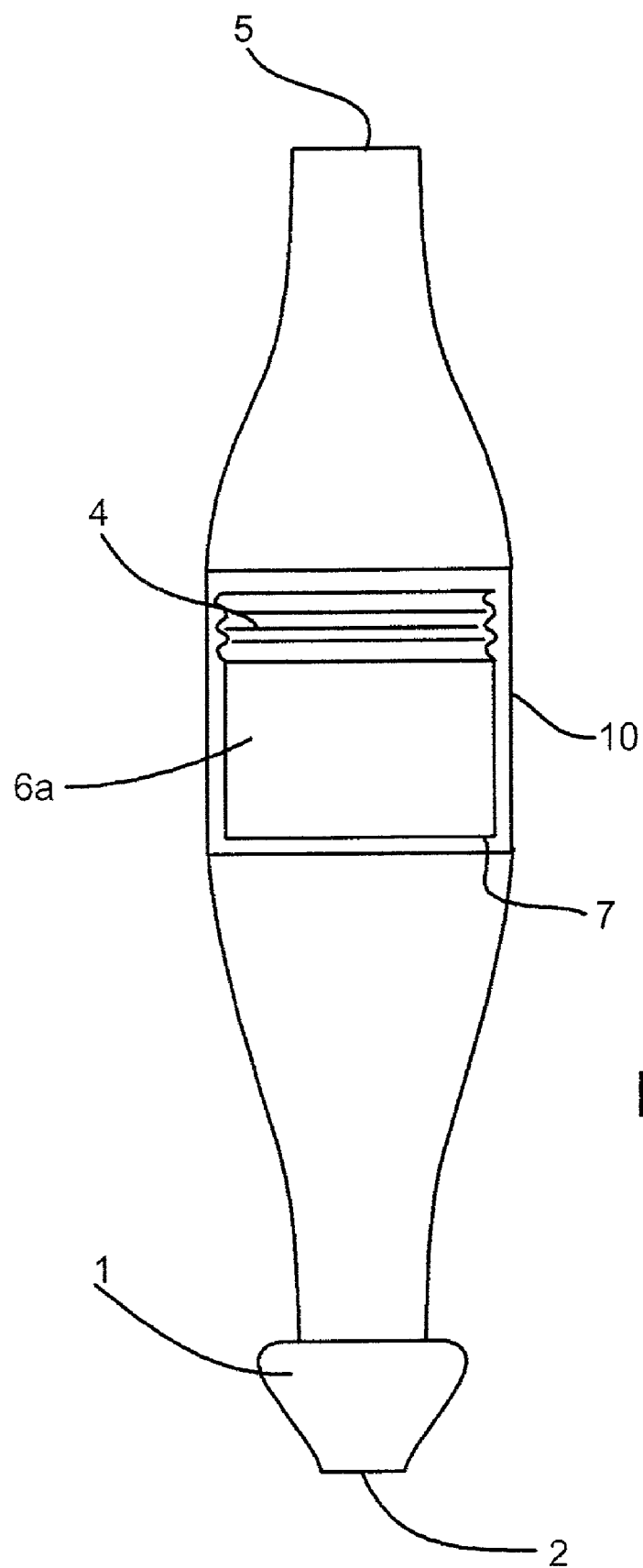
FIG. 4 is a front view of the device of FIG. 1 configured with an attaching member adapted to an opening from which a gas flows.

FIG. 4 is a simplified diagram showing a front view of the device with an attaching member 1 adapted to associate with a circular shaped opening in an object that is to be tested for the inflow or outflow of gas. The attaching member 1 is circular in shape with an outside diameter diminishing in size from its proximal end to its distal end so that it may be inserted into the circular shaped opening until its increasing diameter can no longer enter the opening but rather forms a pressurewise seal within the opening.

Figure 5:
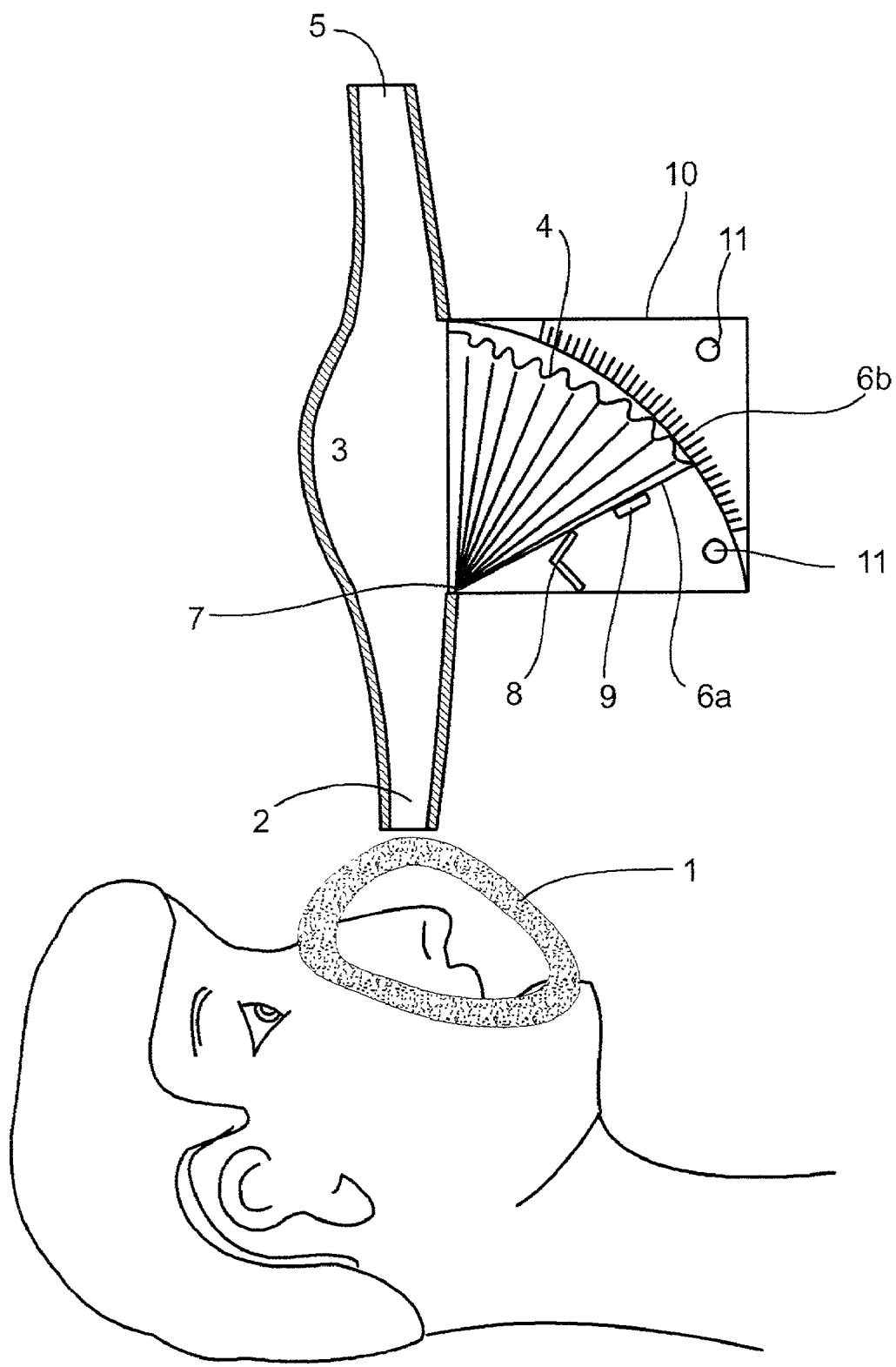
FIG. 5 is a side view of the device of FIG. 1 configured with an attaching member adapted to the nose and mouth of a subject.

FIG. 5 is a section view depicting the device with an attaching member 1 adapted to associate with the mouth and nose of a person.

A device constructed In accordance with the preferred embodiment works on the principle of pressure differential. Detection of gas flow is based on the existence of a difference between a pressure within the chamber 3, which is in communication with the opening being tested, and the ambient pressure outside the chamber 3.

The attaching member 1 of the device, which bears the inlet 2, is applied to the opening to be tested. In the described preferred embodiment, the inlet 2 of the chamber 3 has a greater flow capacity than the outlet 5 of the chamber 3. Therefore, the inflow or outflow of gas, which passes freely through the inlet 2 but is restricted by the outlet 5, causes a difference in the pressure within the chamber 3 relative to the pressure outside the chamber. If gas is flowing into the opening, the restricted flow of the outlet 5 relative to the inlet 2 will cause reduced pressure within the chamber 3. If gas is flowing out of the opening, the restricted flow of the outlet 5 relative to the inlet 2 will cause increased pressure within the chamber 3. This pressure differential continues as long as the flow of gas continues. If the flow stops, the pressure quickly equalizes, as the interior of the chamber 3 is in fluid communication with the ambient pressure outside of the chamber 3 via the outlet 5 of the chamber 3.

The pressure displaceable member 4 of the preferred embodiment of the device is a flexible bellows shaped membrane that is easily deflected. One side of the membrane is exposed to the interior of the chamber 3 and the other side of the membrane is exposed to the ambient pressure. Accordingly, reduced pressure within the chamber 3 causes the membrane to deflect inwards toward the interior of the chamber 3. Increased pressure within the chamber causes the membrane to deflect outwards toward the exterior of the chamber 3. When the membrane is subject to equal pressure on both of its sides, it does not deflect in either direction.

It will be understood that the difference in pressure between the interior of the chamber 3 and the ambient pressure will be influenced by the magnitude of the difference between the rate of flow via the inlet 2 and via the outlet 5. Given the same rate of flow, if the inlet 2 and the outlet 5 are restricted to the same degree, the difference in pressure between the interior of the chamber 3 and the ambient pressure will be less and of shorter duration than if the outlet 5 is restricted to a greater degree than the inlet 2. Accordingly, the sensitivity of the device can be adjusted by increasing or decreasing the difference in the flow capacities between the inlet 2 and the outlet 5.

The pressure displaceable member 4 is coupled to a visual indicator 6. The visual indicator 6 comprises a movable element 6a, which in the described preferred embodiment is configured as a hinged plate, and an adjacent scale 6b. The displacement of the pressure displaceable member 4 is directly communicated to the visual indicator 6, thereby enhancing its visibility. Moreover, the displacement of the movable element 6a registers on the adjacent scale 6b providing a rudimentary means of judging the magnitude of the gas flow.

There is provided a means of applying resistance to the movement of the visual indicator 6 in order to test for the existance of a flow of a certain desired magnitude. A calibrated spring 8 of predetermined tension is used to adjust the resistance of the visual indicator.

A displacement sensor 9 may be attached to the visual indicator for the purpose of increasing the perceptibility of the movement of the pressure displaceable member 4. The sensor 9 may be of the type that emits a visual, audible or tactile signal or that transmits a signal to a remote receptor.

The pressure displaceable member 4, being fragile, is enclosed by a casing 10 which protects it from inadvertent manipulation or injury. The casing 10 contains holes 11 therein so that the outer face of the pressure displaceable member 4 is exposed to the ambient pressure.

While the illustrated embodiments depict the device as having an attaching member 1 configured as a circular plug for engaging a circular hole in an object (FIG. 4), or as a face mask adapted to be applied to the mouth and nose of a subject (FIG. 5), it is to be understood that the present invention is not limited to these particular applications. On the contrary, the present invention contemplates that the attaching member 1 may be adapted to any opening into which or out of which a gas may flow. The attaching member 1 may have any shape, pattern, form or configuration so long as it communicates the interior of the chamber 3 to the opening being tested. The invention may therefore be adapted to detect gas flow from openings in surfaces, in objects, or along the length or at the end of tubes, hoses and pipes and from holes, cracks, ruptures, apertures or breaches of any size or shape. The device may be employed by being held in a stationary position or by being moved over the surface of an object such as a pipe in order to scan for leaks.

Moreover, the device is not defined by a fixed size. On the contrary, devices of different sizes will be required for different applications. It is believed that one practiced in the art will be capable of so adapting the present invention to any application that includes an opening that emits or intakes a gas.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather, the scope of the present invention is defined by the appended claims and includes both combinations and subcombinations of the various features described hereinabove as well as variations and modifications thereof which would occur to persons skilled in the art upon reading the foregoing description.

The invention claimed is:

1. device for detecting the flow of gas through at least one opening in an object, the device comprising:
   a. an inlet for pressurewise association with said opening for receiving said gas flow;
   b. a chamber having an interior in pressurewise association with said inlet;
   c. an outlet, located downstream of said chamber, and open to ambient pressure, said inlet, said chamber and said outlet being configured together for allowing passage through said device of said gas flow, and
   d. a pressure displaceable member having an inner face exposed to and contiguous with the interior of said chamber and an outer face exposed to the ambient pressure, said pressure displaceable member being a hinged member hingedly mounted along one end within said chamber such that said member is pivotally displaceable about said end as a result of a differential in respective pressures of said chamber interior and said ambient pressure, said displacement being indicative of said gas flow through said device.

2. The device of claim 1 wherein said hinged member carries an indicator element cooperable with a fixed scale for indicating the magnitude of displacement of the hinged member, and thereby the magnitude of the gas flow.

3. The device of claim 2 wherein said chamber is expandable, and said hinged member constitutes a wall of said expandable chamber.

4. The device of claim 3, wherein said expandable chamber including said hinged member is enclosed within a housing having an opening for subjecting the hinged member to ambient pressure.

* * * * *